United States Patent [19]

Hentze

[11] 4,154,085

[45] May 15, 1979

[54] METHOD OF DIFFERENTIAL THERMAL ANALYSIS

[75] Inventor: Günter Hentze, Odenthal, Fed. Rep. of Germany

[73] Assignee: Bayer Aktiengesellschaft, Leverkusen, Fed. Rep. of Germany

[21] Appl. No.: 870,402

[22] Filed: Jan. 18, 1978

[30] Foreign Application Priority Data

Feb. 5, 1977 [DE] Fed. Rep. of Germany ....... 2704871

[51] Int. Cl.² ............................................. G01K 17/04
[52] U.S. Cl. ................................................... 73/15 B
[58] Field of Search ................... 73/15 B; 23/230 PC

[56] References Cited

U.S. PATENT DOCUMENTS

| | | | |
|---|---|---|---|
| 2,705,417 | 4/1955 | Romo et al. | 73/15 |
| 2,896,442 | 7/1959 | Bailly | 73/15 |
| 3,022,664 | 2/1962 | Stolwijk | 73/15 |

*Primary Examiner*—Herbert Goldstein
*Attorney, Agent, or Firm*—Sprung, Felfe, Horn, Lynch & Kramer

[57] ABSTRACT

In a method of differential thermal analysis (DTA), an original sample is divided into at least two part samples and one or more part samples are tempered at temperatures below the lowest temperature occurring during DTA at the beginning of decomposition. The differential thermal analysis is then carried out on tempered and untempered samples and the DTA curves are compared with each other.

3 Claims, 6 Drawing Figures

METHOD OF DIFFERENTIAL THERMAL ANALYSIS

The invention relates to a method of differential thermal analysis (DTA) which involves heating a sample at a constant rate of heating and continuously measuring the reaction heat or decomposition heat of the sample. DTA is in principle a dynamic method of measuring, and the dynamics of the measuring method are predetermined by the heating rate of the DTA furnace. This may be for example, of the order of magnitude of from 1° C. min$^{-1}$ to 20° C. min$^{-1}$. Because of the dynamic nature of the measuring procedure, the temperature at the beginning of a reaction or decomposition is altered to a higher temperature by an unpredictable difference in temperature. The change in temperature can be as much as 150° C. in particularly difficult cases. In such cases, no information can be obtained by DTA about the temperature at which the reaction or the decomposition begins.

According to the invention there is provided a method of differential thermal analysis in which a sample is heated at a constant heating rate and the reaction or decomposition heat occurring in the sample is measured continuously, wherein an original sample is divided into at least two part samples, one or more part samples are tempered at temperatures below the lowest temperature at which decomposition begins during differential thermal analysis, and the differential thermal analysis of tempered and untempered samples are compared with each other. In many cases, it may be informative to temper the various part samples at different temperatures or at the same temperatures for different periods. The evaluation of the DTA is obtained by determining the difference of the areas for the reaction heat or decomposition heat of the untempered and the tempered samples. In this way, the effect of a thermal load on the sample may be determined as a function of temperature and time.

Figure 1:
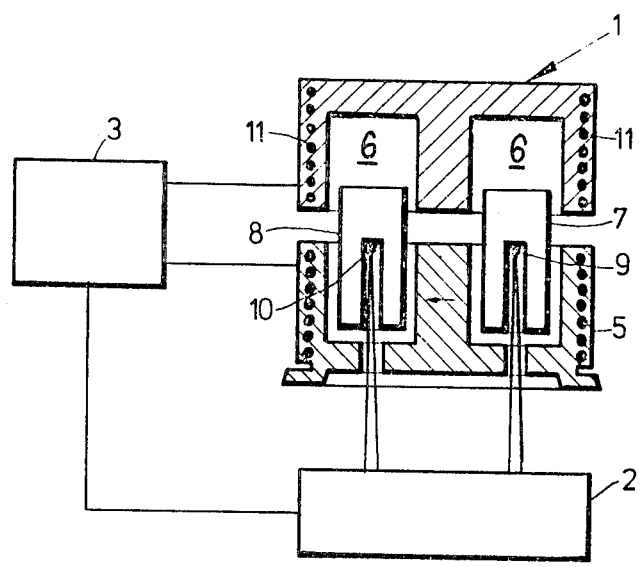
FIG. 1 shows the measurement principle of differential thermal analysis.

FIG. 1 shows a DTA measuring arrangement which comprises a furnace 1, a measuring and recording component 2 and a control instrument 3. In this case, the furnace 1 comprises two symmetrical sections, an upper section 4 and a lower section 5. The sections of the furnace define together symmetrical chambers 6 for receiving a sample container 7 and a comparison container 8. Thermoelements 9 and 10 project into the two containers 7 and 8 and signals from them are amplified and fed to a potentiometer-type recorder 2. The substance in the comparison container does not undergo a thermal reaction in the temperature range to be tested. The heating rate is regulated by the control instrument so that the temperature in the comparison container increases linearly with time. For this purpose, the external shell of the furnace 1 is provided with filament windings 11 which are fed by the control instrument 3. If an endothermic or exothermic reaction takes place in the sample in container 7, the temperature of the sample will be respectively below or above that of the substance in the comparison container. The potentiometer-type recorder 2 records this difference in temperature. The desired DTA diagram is obtained by plotting this temperature difference against the instantaneous value of the temperature.

Figure 2A:
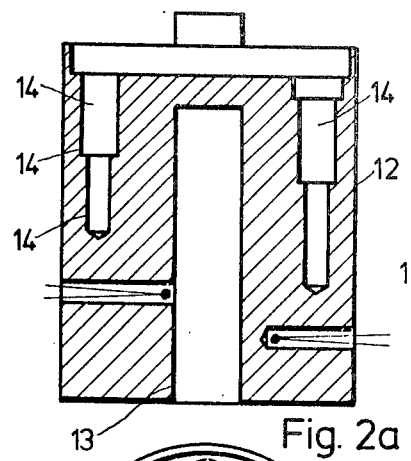
FIG. 2 shows a tempering furnace for tempering several samples at the same temperature including FIG 2b showing a top view and FIG. 2a which is a cross sectional view.
Figure 2B:
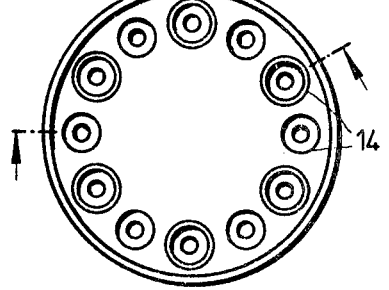
Figure 3:
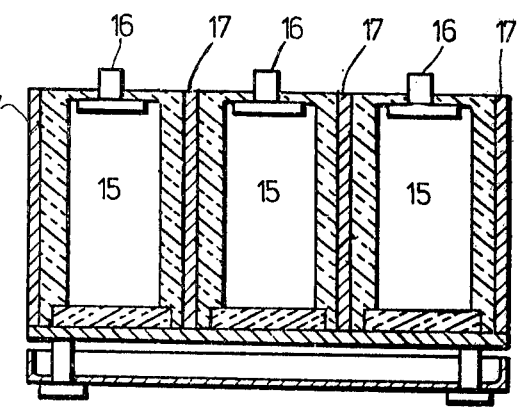
FIG. 3 shows a furnace for tempering at different temperatures.

The arrangement described with reference to FIG. 1 is used for successively analysing tempered and untempered samples. Tempering advantageously takes place in a furnace as shown in FIGS. 2 and 3. As shown in FIGS 2a and 2b the tempering furnace comprises a cylindrical aluminium block 12 which has a bore-hole 13 in the centre for receiving a heating cartridge. A large number of bore-holes 14 for receiving the sample containers are located in concentric circles about the centre of aluminium cylinder 12 on the circumference of the circular surface. These bore-holes are adapted to the shape of the sample containers, which may be, for example aluminium capsules, glass ampoules, small metal flasks etc., and may therefore have various diameters and depths. Each bore-hole 14 advantageously has a plurality of steps (14a, 14b) so that it can receive various sizes of container. A number of samples may be tempered open or closed in one operation at one temperature in a furnace of this type. Alternatively, samples may be tempered independently of each other at different temperatures using the tempering furnace according to FIG. 3. The individual furnaces 15 in FIG. 3 have separate heaters and each may be sealed with a cover 16. The individual furnaces are thermally insulated from each other by means of asbestos coating 17. The furnaces are adjusted to the desired temperatures which are maintained constant by means of an electronic temperature control.

EXAMPLE

Figure 4:
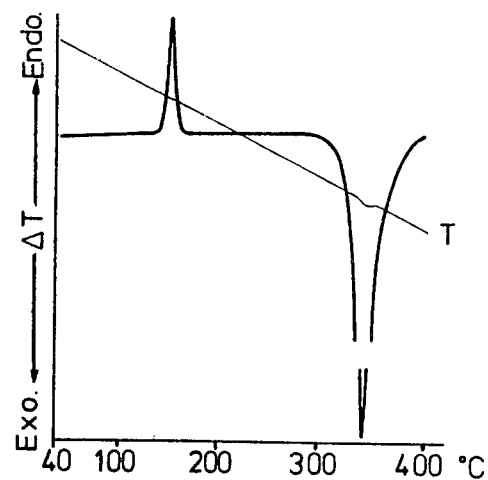
FIG. 4 shows a DTA curve for p-nitroaniline.
Figure 5:
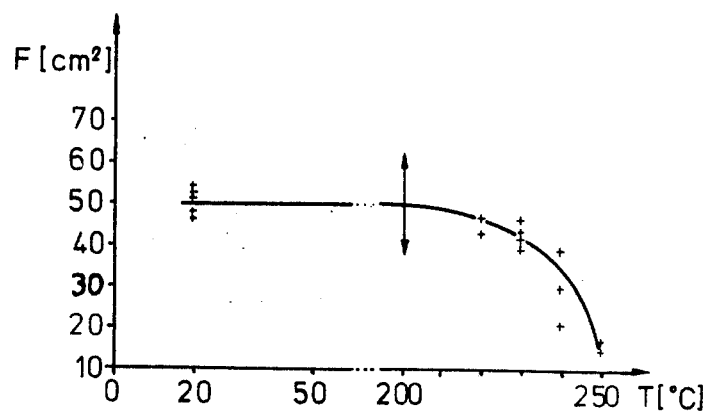
FIG. 5 shows the area of the decomposition peak in the DTA curve according to FIG. 4.

The decomposition behaviour of p-nitroaniline was determined by the tempering method. For this purpose, untempered samples were tested by DTA (FIG. 4). The area of the decomposition peak was then determined and plotted as shown in FIG. 5 which shows F (T) (area of the decomposition peak as a function of the temperature over a constant period) at 20° C. Further samples were tempered for 24 hours at 220° C., 230° C., 240° C. and 250° C. Part of the product decomposes during this tempering. When the tempered samples and the untempered samples were examined by DTA, it was found that the areas of decomposition became smaller. If the remaining areas of decomposition are plotted in the diagram F (T) a clear qualitative determination of the decomposition behaviour of the product is obtained as a function of the temperature for a constant period of heating. If the temperatue is selected as a parameter, decomposition behaviour may be determined as a function of time. The additional effect of catalysts may also be determined in this way.

What we claim is:

1. A method of differential thermal analysis in which a sample is heated at a constant heating rate and the reaction or decomposition heat occurring in the sample is measured continuously, wherein an original sample is divided into at least two part samples, one or more part samples are tempered at temperatures below the lowest temperature at which decomposition begins during differential thermal analysis, and the differential thermal analysis of tempered and untempered samples are compared with each other.

2. A method according to claim 1, wherein the various part samples are tempered at different temperatures.

3. A method according to claim 1, wherein the various part samples are tempered at the same temperature for different periods.

* * * * *